United States Patent
Schaub et al.

(10) Patent No.: US 7,053,135 B2
(45) Date of Patent: May 30, 2006

(54) TWO-COMPONENT DENTAL MOLDING COMPOSITION HAVING AT LEAST ONE ANTI-ACID ACTING COMPOUND

(75) Inventors: Matthias Schaub, Düsseldorf (DE); Klaus-Dieter Nehren, Dormagen (DE); Michael Freckmann, Köln (DE); Holger Urbas, Krefeld (DE)

(73) Assignee: Heraeus Kulzer GmbH & Co.KG, Hanau (DE)

( * ) Notice: Subject to any disclaimer, the term of this patent is extended or adjusted under 35 U.S.C. 154(b) by 220 days.

(21) Appl. No.: 10/637,382

(22) Filed: Aug. 7, 2003

(65) Prior Publication Data

US 2004/0146713 A1    Jul. 29, 2004

(30) Foreign Application Priority Data

Sep. 24, 2002    (DE)    ................. 102 44 693

(51) Int. Cl.
A61F 2/00    (2006.01)
A61C 5/00    (2006.01)

(52) U.S. Cl. .................. 523/115; 523/113; 433/215
(58) Field of Classification Search ........... 523/115, 523/113; 433/215
See application file for complete search history.

(56) References Cited

U.S. PATENT DOCUMENTS

| | | | |
|---|---|---|---|
| 3,453,242 A | 7/1969 | Schmitt et al. ........... 260/77.5 |
| 4,857,623 A | 8/1989 | Emmerling et al. ........... 528/28 |
| 4,877,854 A | 10/1989 | Hattori et al. ............... 528/155 |
| 5,086,148 A | 2/1992 | Jochum et al. ................ 528/15 |
| 5,118,290 A | 6/1992 | Müller et al. ................. 433/48 |
| 5,457,950 A | 10/1995 | Ballhausen et al. ........... 57/308 |
| 6,218,461 B1 | 4/2001 | Schwabe et al. ............ 524/588 |
| 6,310,170 B1 | 10/2001 | Johnston et al. ............... 528/38 |
| 6,383,279 B1 | 5/2002 | Eckhardt et al. ........... 106/38.2 |
| 6,503,994 B1 | 1/2003 | Nehren et al. ................ 528/17 |
| 6,613,860 B1 * | 9/2003 | Dams et al. ................... 528/36 |
| 6,835,760 B1 * | 12/2004 | Schaub et al. .............. 523/109 |
| 2002/0156149 A1 * | 10/2002 | Schaub et al. .............. 523/109 |
| 2003/0083399 A1 | 5/2003 | Schaub et al. .............. 523/115 |
| 2003/0153726 A1 | 8/2003 | Eckhardt et al. ............ 528/423 |

FOREIGN PATENT DOCUMENTS

| | | |
|---|---|---|
| AU | 746131 | 10/1999 |
| DE | 17 45 810 | 5/1963 |
| DE | 36 29 237 | 3/1988 |
| DE | 37 41 575 | 6/1988 |
| DE | 38 38 587 | 5/1990 |
| DE | 43 08 024 | 3/1994 |
| DE | 44 39 769 | 5/1996 |
| DE | 198 08 557 | 9/1999 |
| DE | 100 18 918 | 11/2001 |
| DE | 100 26 857 | 12/2001 |
| DE | 101 04 079 | 8/2002 |
| EP | 0 173 085 | 3/1986 |
| EP | 0 231 420 | 8/1987 |
| EP | 0 269 819 | 6/1988 |
| EP | 0 901 785 | 3/1999 |
| EP | 1 081 191 | 3/2001 |
| EP | 1 226 808 | 7/2002 |
| WO | WO 99/48942 | 9/2000 |
| WO | WO 01/79328 | 10/2001 |

* cited by examiner

Primary Examiner—Tae H. Yoon
(74) Attorney, Agent, or Firm—Norris McLaughlin & Marcus PA

(57) ABSTRACT

Two-component preparation on the basis of silane functionalized polyether derivatives, which cures into an elastomer product after the mixing of a base component containing silane functionalized polyether derivate with a catalyst component containing organic or inorganic acid, wherein the base component comprises an antiacid.

16 Claims, No Drawings

TWO-COMPONENT DENTAL MOLDING COMPOSITION HAVING AT LEAST ONE ANTI-ACID ACTING COMPOUND

This invention relates to two-component preparations, especially those for dental moldings, as well as their use.

BACKGROUND OF THE INVENTION

Different types of preparations for dental molding are generally known (see R. G. Craig, Restorative Dental Materials, The C.V. Moosbe-Company, St. Louis, Toronto, London, 1980, page 1979 and following pages). Overall, high demands are made on such materials (compare K. Eichner, Dental Materials and their Processing, Volume 1, A. Hüthig Publishers, Heidelberg, 4$^{th}$ Edition, 1981, page 45 and following pages):

1. A pleasant odor, taste, and esthetic appearance.
2. The compounds may not contain any toxic or irritating components.
3. The compounds must have a storage stability of several months.
4. The compounds must be capable of being produced economically, and must result in a precise mold.
5. The compounds must be easy to handle.
6. The curing characteristics must meet the clinical requirements.
7. The cured compounds must be resilient and may not deform under continuous tensile force.
8. The cured compounds must have sufficient compression strength and may not break.
9. The cured compounds must be dimensionally stable at room temperature and normal humidity for such a time that exact plaster casts can be produced in a reasonably adequate amount of time.
10. The cured compounds may not cause any plaster damage and must be compatible with other mold compounds.

From the group of different materials, elastomer molding materials are especially beneficial, among other reasons also due to their advantageous application technical and mechanical properties as opposed to the non-elastomer molding materials.

Generally, these elastomer molding materials exist as pastes before their "setting" (i.e., the forming of the elastomer structure), which usually consist of two components (frequently called base paste and catalyst or curing paste), and which set into elastomer after the mixing (cross-linking) process.

Various types of elastomer molding materials are known, such as elastomers with a polysiloxane chain structure, which set with alkoxysilane cross-linking agents (so-called C-silicones) from hydroxyl-functional polysiloxanes by means of condensation reaction, or additive cross-linking polysiloxanes (so-called A-silicones), which react with each other by means of hydrosilization reaction of vinyl groups on a polymer containing polydiorganyl groups (vinyl polymers) with a polydiorganosiloxane containing SiH groups (SiH cross-linking agent), thereby forming an elastomer.

Elastomer molding compounds on the basis of polyether derivatives have also long been known in dentistry, such as the frequently used aziridine polyethers (such as described in DE-B-17 45 810), or additive cross-linking polyether materials, as they are described for instance, in DE-A1-37 41 575 or DE-A1-38 38 587. Polyether molding materials with acrylate or methacrylate groups are known from, for instance, EP 0 173 085.

Dental molding compounds on the basis of silane functionalized polyether derivatives are also known. EP 0 269 819 B1 describes the use of poly additive products comprised of blends containing ether, urethane, and urea groups, together with alkoxy silane groups for the production of molding or duplicating compound in dentistry.

Very similar systems are disclosed in DE 43 08 024 and DE 44 39 769, namely plastics with at least one poly additive product containing silane, ether, and urethane groups, and possibly urea groups, with a predominantly linear molecule structure and predominantly aliphatic or cycloaliphatic linked ether or urethane segments, and a rate median of molar mass within the range of 800–20000, with a content of terminally arranged silyl groups, whereby at least one ether group is present in at least one of the substituents at the silicon atom.

Finally, DE 101 04 079.2-42 describes blends on the basis of alkoxysilyl functional polyether with a linear or branched main chain as the molding and duplicating compounds in dentistry. Furthermore, silane functionalized polyether derivatives are also known as additives for the activator components of condensation cross-linking silicon compounds. Such systems are described in DE 198 08 557.

In addition to thinners, fillers, and additional modifiers, molding compounds on the basis of silane functionalized polyether derivatives according to prior art contain acid compounds and water as the catalytically active components in the catalyst components. In the case of blends of base and catalyst, a cross-linking, and therefore the transition into the elastomer condition occurs by means of acidic catalyzed hydrolysis and condensation reactions at the silane end groups. Due to the content of an acidic compound and of water in the catalyst component, the curing properties may be adjusted to the clinical requirements.

Processing time, i.e., the time period between the completion of mixing and the beginning cross-linking process (transition of the compound from the plastic into the elastic phase, characterized by strongly reduced flow capability, roping), and the setting time (time period between the completion of mixing and the processability of the cured compound, for instance by means of oral removal) of the molding compound are key parameters for the user. Usually, base and catalyst components are adjusted to each other in such a way that processing times are set within a range of 30 s to 3 min. The setting times are usually a maximum of 7 min.

Molding compounds suitable for practical applications must have a storage stability of several months, i.e., physical properties, such as the viscosity, the processing and setting times may not substantially change within this time period. Storage stability over a period of 2 to 3 years is desirable.

The molding compounds may also be temporarily exposed to increased temperatures during storage and transport. Increased temperatures generally reduce storage stability. From experience, molding compounds should remain stable, or able to be processed, for at least one week at a storage temperature of 60° C.

The base components according to prior art, which contain silane functionalized polyether derivatives, however, have the distinct disadvantage of a viscosity increase during storage due to their sensitivity to moisture and acidic conditions. Storage at room temperature has the approximate effect of doubling the base viscosity within several months. This effect occurs at an accelerated rate at increased temperatures.

The storage at 60° C. usually causes very highly viscous or branched products after one week, which then can no longer be processed.

Therefore, the need exists for preparations on the basis of silane functionalized polyether derivatives, which have a setting behavior that is suitable for practical applications after blending with acidic catalysts (i.e., processing times of 0.5 to 3.5 min at room temperature, and setting times, according to which oral removal is possible, of a maximum of 7 min after the beginning of the mixing process) on one hand, and which as an individual component have a substantially extended storage stability, or only a slight viscosity increase at increasing storage duration as opposed to prior art, on the other hand.

Systems are known from the area of moisture-curing adhesive and sealing compounds, which are also formulated on the basis of silane functionalized polyether derivatives (for example DE 36 29 237). Analogous to dental molding compounds, the requirements of a sufficiently long shelf life exists with these systems. It is therefore often reasonable to stabilize such preparations from for instance, penetrating moisture in order to increase shelf life. As described in WO99/48942, such an improvement of shelf life can be achieved by means of using moisture stabilizers. Accordingly, all compounds that react with water with the formation of inert groups are suitable as moisture stabilizers as opposed to reactive groups present in the preparation, and which thereby undergo preferably little changes in their molecular weight. Additionally, the reactivity of the stabilizers as opposed to the moisture penetrating the preparation must be higher than the reactivity of the end groups of the silane functionalized polyether derivative present in the preparation. Agents suitable as moisture stabilizers are for instance isocyanates or silanes, such as vinyl silane, oxime silane, or benzamide silane.

The use of additional additives, such as amines, is known from the area of moisture-curing adhesive and sealing compounds on the basis of silane functionalized polyether derivatives. Amines are used as catalysts for the acceleration of the curing speed (see WO 99/48942, U.S. Pat. No. 6,310,170).

Specific sterically hindered amines are used as UV stabilizers, for instance, in a concentration range of up to 2% (so-called hindered amine light stabilizers, or HALS).

For dental molding compounds and moisture-curing adhesive and sealing compounds on the basis of silane functionalized polyether derivatives, the use of various fillers is known, such as silica dust, cristobalite dust, calcium sulfate, diatomaceous earth, silicates, pyrogenetic or precipitated silicon dioxide, chalk, lime dust, zeolite, bentonite, glass sphere glass dust, fiber glass, and fiber glass short sections, soot.

In order to formulate two-component, acidic-curing preparations on the basis of silane functionalized polyether derivatives according to prior art, antiacid acting fillers or additives, such as chalk, lime dust, zeolite, alkali silicates, or diatomaceous earth are generally not used in order to avoid the risk of neutralization of the acidic catalyst component, and therefore a delayed curing process.

The invention is based on the task of providing an improved preparation as opposed to prior art.

SUMMARY OF THE INVENTION

The task is solved according to the invention by means of a two-component preparation that sets at room temperature into an elastomer material, consisting of a base component (A) and a catalyst component (B) containing acid, whereby A contains at least one silane functionalized polyether derivative, at least one antiacid acting compound, and possibly additional additives.

In a preferred embodiment, A contains at least 5–95% of the silane functionalized polyether derivative, 0.002–15% of at least one antiacid acting compound, 0–90% of an inert thinner, 0–60% of additional modifiers.

The invention also relates to the use of the described two-component preparation that sets at room temperature into an elastomer material. Preferably, the presentation of the components (A) and (B) occurs in the form of tubes, cans, tubular bags, or double cartridges.

It was surprisingly found that preparations on the basis of silane functionalized polyether derivatives, which contain at least one antiacid acting compound, and possibly additional additives in the base component (component A), have a significantly increased shelf life, and at the same time may have physical properties suitable for practical applications, especially also regarding the setting behavior. The invention is targeted on a two-component composition on the basis of silane functionalized polyether derivatives, which can cure to an elastomer product after mixing a base component (component A) containing silane functionalized polyether derivatives with an acidic catalyst component (component B) at room temperature.

The invention particularly relates to such preparations on the basis of silane functionalized polyether derivatives, which are characterized by suitable processing times and setting times after the mixing with the catalyst component, and therefore have a long shelf life as individual components.

Surprisingly it was found that preparations containing antiacid acting compounds in those concentration ranges that are suitable for the extension of shelf life, may still have processing and setting times suitable for practical application after the mixing with catalyst components.

DETAILED DESCRIPTION

By adjusting the acid concentration of the catalyst components, the antiacid acting component of the base paste can be balanced in certain concentration ranges so that the application technical processing and setting times desired can be adjusted. In reverse order, the concentration of the antiacid acting compounds can also be adjusted to the acidic component within a certain framework in such a way that the application technical processing and setting times desired are adjusted.

The amount of antiacid acting compound(s) included in component A is 0.0001–60% wt, preferably of 0.002–15% wt.

Furthermore, it was surprisingly found that by adding special antiacid acting compounds, such as amines that are used according to prior art to accelerate the curing speed of preparations with silane functionalized polyether derivatives, an extension of shelf life (by means of reducing the viscosity increase observed with increasing shelf duration) can be achieved. In addition to amines, many other antiacid acting compounds, if used as additives to the base component, also have an extending effect on storage stability.

The antiacid acting compounds are preferably selected from the following groups: alkaline or amphoteric oxides, hydroxides, carbonates, carboxylates, alkaline organic compounds with N, As, O, P, S, or Sb as the hetero-atom.

Also preferred are organic compounds with isocyanate, epoxide, carbodiimide, or aziridine groups as antiacid acting compounds.

It is further preferred if organic compounds containing nitrogen are used as antiacid acting compounds.

The preparations according to the invention on the basis of silane functionalized polyether derivatives, which can be used for molding for instance in dentistry, are generally formulated as two-component systems consisting of a component A, and of a component B.

Component A contains as the key component for the elastomer structure a silane functionalized polyether derivative, or a mixture of several silane functionalized polyether derivatives varying in molecular weight and/or chemical structure.

Suitable silane functionalized polyether derivatives are polymers, which are characterized by the combination of the structural characteristic of the polyether chain with the structural characteristic of a reactive silane end, and/or silane side group. These reactive silane end, and/or silane side groups are characterized by groups that can be hydrolyzed, and/or by hydroxyl groups at the Si atom.

Suitable silane functionalized polyether derivatives can be, for instance pure polyethers, which are terminally functionalized with alkoxy silyl residues, such as the polyether derivatives known as "modified-silane polymers" (MS Polymer®).

Especially suitable silane functionalized polyether derivatives are silane terminated polyurethane groups, and the silane functionalized polyadditive products containing ether, urethane, and urea groups known from EP 0 269 819 B1, or the alkoxy silyl functional polyether with linear or branched main chain known from DE 101 04 079.2-42.

But suitable silane functionalized polyether derivatives can also be based on copolymers of polyethers with other polymers, such as polyester, polyolefin, or polyorganosiloxane.

Therefore, the silane functionalized polyether derivative preferably contains urethane groups, or urea groups, or trialkoxy silyl or alkyldialkoxy silyl groups.

In addition to the silane functionalized polyether derivative, the component A of the preparation according to the invention also contains an antiacid acting component, or a mixture of several antiacid acting components. Suitable antiacid acting compounds are generally inorganic or organic compounds, which are able to neutralize acids, such as oxide, hydroxide, carbonate, carboxylates of certain metals with alkaline or amphoteric character, as well as alkaline organic compounds with N, As, O, P, S, or Sb as the hetero-atom. Of the alkaline organic compounds, amines and heterocycles containing nitrogen, such as, for instance, alkaloids are particularly preferably used as antiacid components. Finally, the silane functionalized polyether derivatives themselves can act as an antiacid component with suitable functionalizing, such as with amino groups.

Furthermore, antiacid acting compounds in the sense of this invention are such compounds that enter into an additive reaction with acids, such as isocyanates, carbodiimides, epoxides, or aziridines.

Inorganic fillers, which are surface-functionalized with antiacid acting organic compounds, are also suitable as antiacid acting components. Especially preferred are fillers, which are loaded with amino, isocyanate, epoxide, carbodiimide, or aziridine groups.

The antiacid acting compound in component A is preferably used within a concentration range of 0.0001–60% by weight. Especially preferred are concentrations of between 0.002–15% by weight.

Both component A and component B may contain additional common modifiers, such as thinners, softeners, fillers, dies, pigments, odor or flavor additives, thixotroping agents, emulsifiers, stabilizers.

The catalyst component (component B) contains as the catalytically active compound an organic and/or inorganic acid, or mixtures of various organic and/or inorganic acids, as well as water. Sulphonic acids are preferably used, especially preferred is 4-toluene sulphonic acid. It is also preferred if the catalyst component (B) contains water. The use of several acids can be helpful for the adjustment of the setting progress. Furthermore, the use of certain salts, for instance fluorides, such as sodium fluoride, potassium fluoride, or ammonium fluoride, as well as of organic aminofluorides can also be helpful for the adjustment of the curing behavior.

The production of component A and component B can be performed according to the procedure described in DE 101 04 079.2-42.

Components A and B can be mixed at a ratio of 20:1 to 1:5 for the purpose of processing. Preferably, the components are mixed at a ratio of 10:1 up to 1:1.

Preferably, components A and B are presented in tubes, cans, tubular bags, or as double cartridges.

The following illustrates embodiments of the invention. Base components with different antiacid acting compounds are produced according to DE 101 04 079.2-42 (U.S. Pat. No. 2002/0,156,149A1), example 5, and then loaded into aluminum tubes (see table 1 for compositions). The verification of storage stability at 60° C. shows a substantially lower viscosity increase in the preparations according to the invention as opposed to prior art (see table 2). The preparations from table 1 can be cured within processing times that are suitable for practical application (see table 4) by means of mixing with catalyst components, which have been produced according to DE 101 04 079.2-42 (U.S. Pat. No. 2002/0156149A1), example 3 (see table 3).

TABLE 1

Composition of the base components according to the invention (A1–A6); comparison example: A7

|  | A1 | A2 | A3 | A4 | A5 | A6 | A7 |
|---|---|---|---|---|---|---|---|
| Silane terminated polyether derivative according to EP 0269 819 B1, example 3 | 20,00 | 20,00 | 20,00 | 20,00 | 20,00 | 20,00 | 20,00 |
| Thinner (dibenzyl toluene) | 20,00 | 19,99 | 19,99 | 19,95 | 19,95 | 19,97 | 20,00 |
| Filler (silica dust) | 56,80 | 57,00 | 58,50 | 58,50 | 57,00 | 57,00 | 58,50 |
| Structuring agent | 3.00 | 3.00 | 1.50 | 1.50 | 3.00 | 3.00 | 1.50 |

TABLE 1-continued

Composition of the base components according to the invention (A1–A6); comparison example: A7

|  | A1 | A2 | A3 | A4 | A5 | A6 | A7 |
|---|---|---|---|---|---|---|---|
| Antiacid acting compound: | | | | | | | |
| Alkaline magnesium-aluminum-hydroxy-carbonate, pH 9–10 | 0.20 | | | | | | |
| 3-aminopropyltriethoxy silane | | | | 0.01 | 0.05 | | |
| Polypropylene glycoldiamine, MV 230 | | | | | | 0.05 | |
| 4-hydroxy-2,2,6,6-tetramethyl piperidine | | | 0.01 | | | | |
| 1,8-bis(dimethylamino)-naphthaline | | | | | | | 0.03 |

TABLE 2

Characterization of the storage stability of the base components according to the invention (A1–A6); comparison example: A7

|  | A1 | A2 | A3 | A4 | A5 | A6 | A7 |
|---|---|---|---|---|---|---|---|
| Viscosity (23° C., 3 s$^{-1}$) directly after production [Pas] | 464 | 312 | 292 | 183 | 434 | 444 | 257 |
| Viscosity (23° C., 3 s$^{-1}$) after one week of storage at 60° C. [Pas] | 1960 | 985 | 591 | 262 | 1167 | 2100 | Not measurable, material cured |

TABLE 3

Acid contents of different catalyst components (B1–B3), produced according to DE 101 04 079.2-42, example 3

|  | B1 | B2 | B3 |
|---|---|---|---|
| Weight portion 4-toluene sulphonic acid monohydrate [%] | 0.27 | 0.31 | 0.51 |

TABLE 4

Processing times and shore grades of different mixtures consisting of base and catalyst components, example 7: comparison example

| | Example | | | | | | |
|---|---|---|---|---|---|---|---|
|  | 1 | 2 | 3 | 4 | 5 | 6 | 7 |
| Base component used | A1 | A2 | A3 | A4 | A5 | A6 | A7 |
| Catalyst component used | B1 | B2 | B2 | B2 | B3 | B3 | B2 |
| Weight ratio of base to catalyst component | 5:1 | 5:1 | 5:1 | 5.5:1 | 5:1 | 7:1 | 5:1 |
| Processing time [min:s] | 2:30 | 2:55 | 2:35 | 2:30 | 3:40 | 2:55 | 2:15 |
| Shore A (after 60 min) | 55 | 56 | 58 | 55 | 57 | 58 | 59 |

We claim:

1. A two-component preparation that sets at room temperature into an elastomer material, consisting of a base component (A) and a catalyst component (B) containing acid, wherein A contains at least one silane functionalized polyether derivative, at least one antiacid acting compound, and optionally additional additives.

2. A two-component preparation that sets at room temperature into an elastomer material according to claim 1, wherein the antiacid acting compound is present in component A in an amount of 0.0001–60%.

3. A two-component preparation that sets at room temperature into an elastomer material according to claim 1, wherein A is comprised of at least 5–95% wt of the silane functionalized polyether derivative, 0.002–15% of at least one antiacid acting compound, 0–90% of an inert thinner, 0–60% of additional modifiers.

4. A two-component preparation that sets at room temperature into an elastomer material according to claim 1, wherein the silane functionalized polyether derivative contains urethane groups.

5. A two-component preparation that sets at room temperature into an elastomer material according to claim 1, wherein the silane functionalized polyether derivative contains urea groups.

6. A two-component preparation that sets at room temperature into an elastomer material according to claim 1, wherein the silane functionalized polyether derivative contains trialkoxy silyl or alkyldialkoxy silyl groups.

7. A two-component preparation that sets at room temperature into an elastomer material according to claim 1, wherein the antiacid acting compounds are selected from the group consisting of: alkaline or amphoteric oxides, hydroxides, carbonates, carboxylates and alkaline organic compounds with N, As, O, P, S, or Sb as the hetero-atom.

8. A two-component preparation that sets at room temperature into an elastomer material according to claim 1, wherein organic compounds containing nitrogen are used as antiacid acting compounds.

9. A two-component preparation that sets at room temperature into an elastomer material according to claim 1, wherein organic compounds with isocyanate, epoxide, carbodiimide, or aziridine groups are used as antiacid acting compounds.

10. A two-component preparation that sets at room temperature into an elastomer material according to claim 1, wherein the catalyst component (B) contains 4-toluene sulphonic acid.

11. A two-component preparation that sets at room temperature into an elastomer material according to claim 1, wherein the catalyst component (B) contains water.

12. A dental molding composition comprising the two-component preparation of claim 1.

13. A method of forming a dental molding, which comprises forming said dental molding by mixing the two components of the two-component preparation of claim 1.

14. The method of claim 13, wherein components (A) and (B) are packaged in tubes, cans, tubular bags, or double cartridges prior to mixing.

15. The two-component preparation of claim 2, wherein said amount of antiacid acting compound is from 0.002 to 15% wt.

16. A two-component preparation that sets at room temperature into an elastomer material according to claim 2, wherein
    A is comprised of at least 5–95% wt of the silane functionalized polyether derivative,
    0.002–15% of at least one antiacid acting compound,
    0–90% of an inert thinner,
    0–60% of additional modifiers.

* * * * *